United States Patent [19]
Lindsay

[11] Patent Number: 5,254,080
[45] Date of Patent: Oct. 19, 1993

[54] QUICK-CHANGEOVER APPARATUS FOR HANDLING MEDICAL FLUID

[75] Inventor: Erin J. Lindsay, Manchester, Mich.

[73] Assignee: Minnesota Mining and Manufacturing Company, St. Paul, Minn.

[21] Appl. No.: 686,495

[22] Filed: Apr. 17, 1991

Related U.S. Application Data

[63] Continuation-in-part of Ser. No. 493,286, Mar. 14, 1990.

[51] Int. Cl.$^5$ .............................................. B01D 19/02
[52] U.S. Cl. ........................................ 604/4; 604/319; 604/405; 604/406; 128/DIG. 3
[58] Field of Search ........................................ 604/4-6, 604/317-319, 403, 405, 406, 240, 249, 905; 128/DIG. 3; 137/614

[56] References Cited

U.S. PATENT DOCUMENTS

| | | | |
|---|---|---|---|
| 3,678,959 | 7/1972 | Liposky | 137/625.11 |
| 4,064,909 | 12/1977 | Neward | 137/625.48 |
| 4,432,760 | 2/1984 | Mittleman et al. | 604/246 |
| 4,440,723 | 3/1984 | Gordon | 422/47 |
| 4,568,345 | 2/1986 | Keilman et al. | 604/403 |
| 4,576,199 | 3/1986 | Svensson et al. | 604/905 X |
| 4,617,012 | 10/1986 | Vaillancourt | 604/905 |
| 4,664,682 | 5/1987 | Monzen | 55/178 |
| 4,770,787 | 9/1988 | Heath et al. | 610/647 |
| 4,822,341 | 4/1989 | Colone | 604/175 |
| 4,846,800 | 7/1989 | Ouriel et al. | 604/4 |
| 4,909,780 | 3/1990 | Ouriel et al. | 604/4 |
| 4,988,342 | 1/1991 | Herweck et al. | 604/321 |
| 5,087,250 | 2/1992 | Lichte et al. | 604/321 |

FOREIGN PATENT DOCUMENTS

| | | |
|---|---|---|
| 0312101 | 4/1989 | European Pat. Off. |
| 2135890 | 9/1984 | United Kingdom |

Primary Examiner—Robert A. Hafer
Assistant Examiner—Sam Rimell
Attorney, Agent, or Firm—Gary L. Griswold; Walter N. Kirn; Stephen W. Bauer

[57] ABSTRACT

A connection system for facilitating connections with an apparatus for handling medical fluids, such as blood, to adapt the apparatus for one or more particular uses. The system includes one or more connector blocks having an access opening and at least one connection device, such as a fitting for mounting medical grade tubing, in fluid communication with the access opening, and a seal tray for slidably mounting a connector block and initialy sealing the access opening in the connector block. A track and a part are provided on the apparatus, with the track being adapted to slidably mount the connector block on the apparatus such that the access opening of the block can be moved into and out of alignment with the port. The seal tray and the track are so configured that the seal tray can be aligned with the track to allow the connector block to be moved at least partially off of the sealing tray onto the track, thereby to bring the connector block's access openings into alignment with the port.

23 Claims, 9 Drawing Sheets

QUICK-CHANGEOVER APPARATUS FOR HANDLING MEDICAL FLUID

CROSS REFERENCE TO RELATED APPLICATION

This is a continuation-in-part application of U.S. patent application Ser. No. 07/493,286, filed Mar. 14, 1990, now U.S. Pat. No. 5,149,318.

BACKGROUND OF THE INVENTION

This invention relates to a quick-changeover apparatus for handling medical fluid, and in particular to an apparatus for handling a patient's blood during a medical procedure.

There are instances where one blood handling device would be used for a patient during a medical procedure, and another blood handling or collecting device would be needed for post-procedure care. For example, in the case of heart surgery, a blood reservoir is used as part of the blood recovery and oxygenation system. After the procedure, a separate autotransfusion reservoir might be used to collect the patient's blood from the surgical wound for reuse, and/or another reservoir might simply be used to collect blood drained from the surgical wound for disposal. Several "convertible" devices are available that can be used both as a blood reservoir during surgery and a pleural drainage unit after surgery. These devices provide several advantages: they eliminate the need for dedicated pleural drainage devices; they minimize the amount of disposable equipment that is used (and must be disposed of); they are more economical; and they reduce staff-time associated with setting up multiple devices. Moreover, many of these devices allow for autotransfusion of the collected blood, reducing risk to the patient and reducing the demand for blood products.

However, to varying degrees these devices have also suffered from one significant draw-back: the conversion of these devices from use as a surgical blood reservoir to a drainage unit or to an autotransfusion device is time consuming and complex. Many of these devices come with pages of detailed instructions that the nursing staff is expected to follow to properly disconnect and cap the numerous connectors required for use as a surgical blood reservoir. This increases the pressure on the nursing staff to quickly and accurately make the conversion. Furthermore, each tube connection that must be undone and capped increases the chance of blood splattering the medical staff, with the attendant risk of spreading disease, such as hepatitis and AIDS.

SUMMARY OF THE INVENTION

The invention provides a connection system for facilitating connections with an apparatus for handling medical fluids, such as blood, to adapt the apparatus for one or more particular uses. The invention eliminates most of the detailed disconnecting and capping steps required by the previously available convertible apparatus by providing an apparatus with connector blocks that can simply be removed after use in one mode and replaced by new blocks specially adapted for use in the new mode. All the parts required for use in both modes may be provided on the apparatus. Conversion is a matter of sliding the proper devices into their operative positions.

Generally, the system comprises at least one port means in the apparatus comprising at least one opening in fluid communication with the apparatus, and one or more connector blocks. Each connector block has at least one access opening for fluid communication with the port means, and at least one connection device is provided for making a connection to the connector block to adapt the apparatus for a particular medical use when the connector block is in communication with the port means of the apparatus. A track means is provided on the apparatus for movably mounting the connector blocks on the apparatus such that the blocks moved into and out of alignment with the port means. The system also includes a seal tray for movably mounting a connector block and initially sealing the connector blocks access opening. The seal tray and the track means are so configured that the seal tray can be aligned with the track means to allow the connector block to be moved at least partially off of the sealing tray onto the track means, thereby to bring the connector block's access openings into alignment with the port means.

Preferably, the connection block remains in contact with its sealing tray when the access openings of the connector block are in fluid communication with the port means to hold the sealing tray in position relative to the track means.

The system may also include a first block slidably mounted on the track means, with the first block being initially aligned with the port means but being displaceable therefrom by a connector block. For example, the first block may be adapted to occlude and seal the port means when aligned therewith in order to seal the port before or after use of the apparatus. The system may also be provided with a water seal device connected to the connector block.

The invention thus facilitates sealing the fluid handling apparatus and connector blocks from contamination or leakage before and after the procedure, and provides a convenient way to handle and store connector blocks before and after the procedure. More specifically, the invention facilitates handling the connector blocks and apparatus in such a manner as to reduce the risk of contaminating sterile passageways in the connector blocks and apparatus, and disposing of the connector blocks or apparatus in such a manner as to reduce the risk of leakage of blood or other medical fluid from the connector blocks or apparatus.

The invention may also provide such a system that is adapted to organize a plurality of connector blocks for different medical procedures or practices. For example, various types of connector blocks can be provided on seal trays for use in different procedures or by different medical practitioners. The apparatus could thus be adapted to the need and preferences of medical practitioners.

These and other advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figures 1, 2, 3, 4, 5:
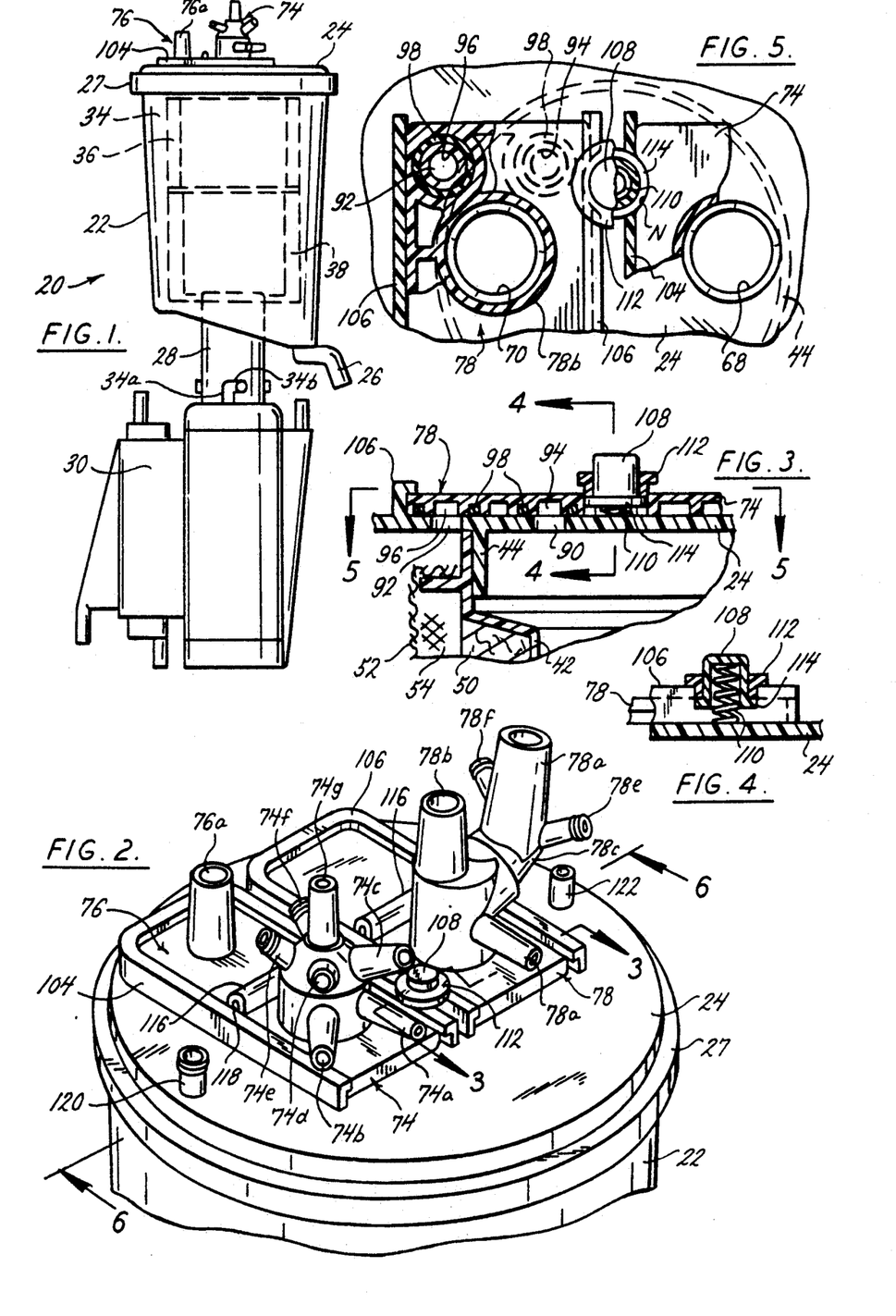
FIG. 1 is a side elevation view of a first embodiment of the present invention in the form of a cardiotomy reservoir.
FIG. 2 is a perspective view of the first embodiment.
FIG. 3 is a partial cross-sectional view of the first embodiment, taken along the plane of line 3—3 in FIG. 2.
FIG. 4 is a partial cross-sectional view of the first embodiment, taken along the plane of line 4—4 in FIG. 3.
FIG. 5 is a partial cross-sectional view of the first embodiment, taken along the plane of line 5—5 in FIG. 3.

A first embodiment of this invention in the form of a surgical blood apparatus is indicated generally as 20 in FIG. 1. The surgical blood apparatus 20 is adapted for use as part of a blood recovery and oxygenation system of the type used during cardiac surgery. However, according to the principles of this invention the apparatus 20 is also convertible for use in blood collection after the surgical procedure. Although described with respect to surgical blood apparatus 20, this invention is not so limited, and could be applied to other apparatus for handling medical fluids during a medical procedure.

Figures 6, 8, 9:
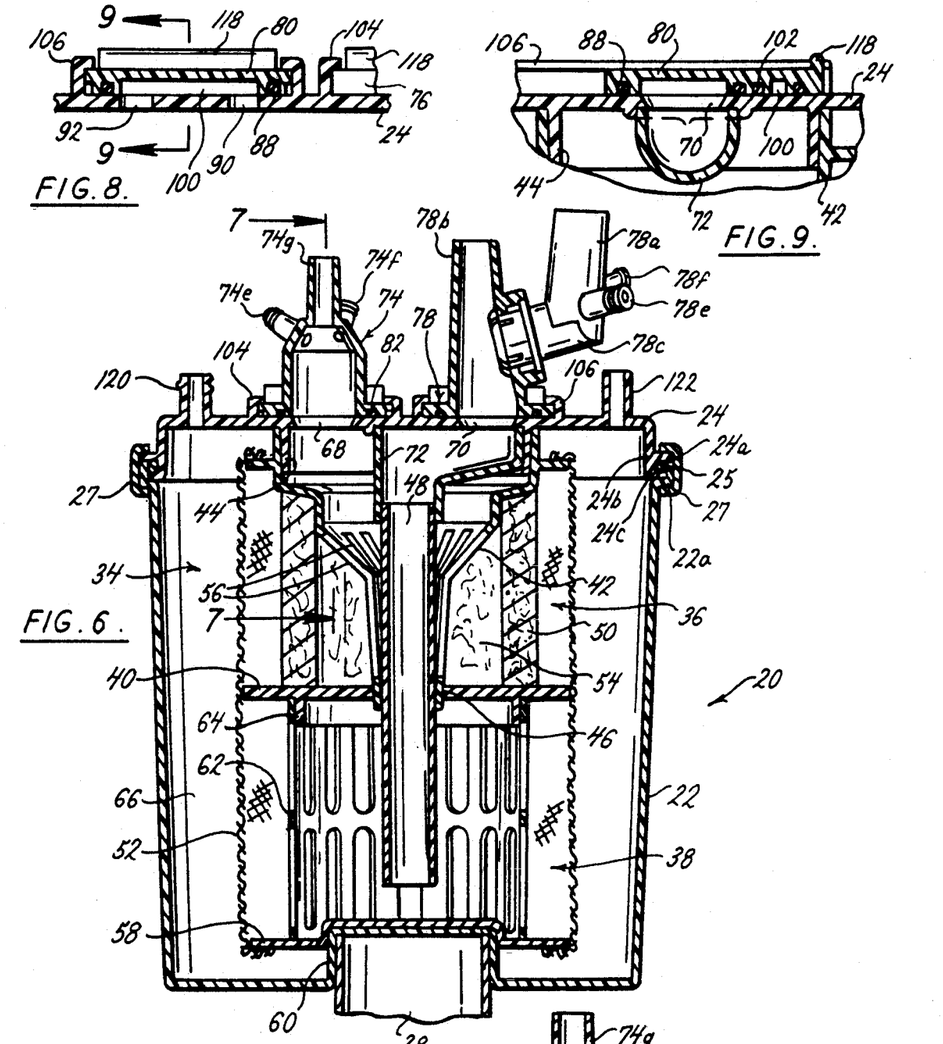
FIG. 6 is a cross-sectional view of the first embodiment, taken along the plane of line 6—6 in FIG. 2.
FIG. 8 is a partial cross-sectional view of the first embodiment, after the fourth device has been moved into alignment with the port means.
FIG. 9 is a partial cross-sectional view of the first embodiment, taken along the plane of line 9—9 in FIG. 8, after the fourth device has been moved into alignment with the port means.
Figure 7:
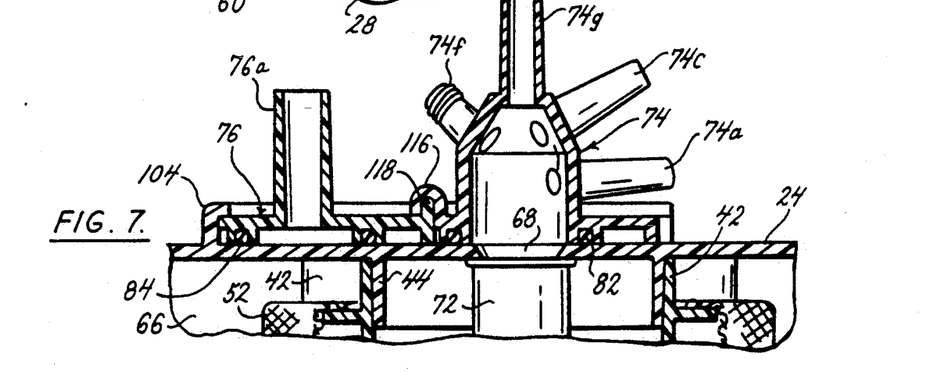
FIG. 7 is a partial cross-sectional view of the first embodiment, taken along the plane of line 7—7 in FIG. 6.

The surgical blood apparatus 20 comprises a reservoir 22 having an open top closed by a lid 24. As best shown in FIG. 6, the reservoir 22 and the lid 24 are constructed to permit the lid 24 to rotate with respect to reservoir 22, while maintaining a seal. The lid 24 has a rim 24a that rests on the top edge of the reservoir 22. A portion 24b of the lid extends into the reservoir 22, and has an annular groove 24c that contains an O-ring for sealingly engaging the interior wall of the reservoir, while permitting relative rotation. A retaining ring 27, having a channel-shaped cross-section, engages both the top of the lip 24a and a shoulder 22a in the reservoir 22, to retain the lid 24 in the reservoir. This mounting allows the lid, and all the connectors thereon to swivel for more convenient handling of the apparatus 20. It will be appreciated that the interior of the apparatus 20 is constructed to allow for this swivel-action. The reservoir 22 has an outlet 26 in its lowermost portion. As is well known in the art, during cardiac surgery the outlet 26 is connected to either a venous reservoir or to a blood pump if the surgical blood apparatus 20 is used as a venous reservoir as well as a cardiotomy combination. After surgery the outlet 26 may be connected to a blood pump to return collected blood to the patient. A hollow cylinder 28 projects from the bottom of the reservoir 22 for mounting the reservoir on to an oxygenator 30. The cylinder 28 may be provided with L-shaped slots 32 by which the apparatus may be releasably secured to the oxygenator 30, with a bayonet-style connection, as described in more detail below.

As is well known in this art, a blood filter/defoamer unit 34 is mounted inside the reservoir 22. As best shown in FIG. 6, the unit 34 comprises an upper blood filtration section 36 and a lower blood defoaming section 38, separated by a generally planar horizontal separating plate 40. The unit 34 is constructed so that blood can be separately provided to the filtration section 36 and to the defoaming section 38.

The blood filtration section 36 comprises a generally funnel-shaped member 42 for receiving blood to be filtered. The mouth of the funnel-shaped member 42 is adapted to fit around an annular support 44 depending from the lower surface of the lid 24. The lower end of the funnel-shaped member 42 is supported in a hole 46 in the center of the plate 40. The member 42 is sealed with the plate 40 to prevent blood from passing from the filtration section 36 to the defoaming section 38. A tube 48 extends axially through the funnel-shaped member 42 to the defoaming section 38, and is sealed with the lower end of the funnel-shaped member 42 to prevent blood from passing from the funnel-shaped member 42 into the defoaming section 38.

The funnel-shaped member 42 is surrounded by a generally cylindrical filter member 50. The top of the filter member 50 abuts the funnel-shaped member 42 and the bottom of the filter member 50 abuts the plate 40, defining a filtration chamber 54 between the filter member 50 and the funnel-shaped member 42. The body of the funnel-shaped member 42 has a plurality of radially extending slots 56 therein so that blood provided to the funnel-shaped member passes to the filtration chamber 54. The blood can then pass through the filtration member 50, which removes clots and debris, etc. There is a defoamer mesh sock 52 that extends the entire height of unit 34.

The defoamer section 38 comprises a base plate 58 supported on a cylindrical projection 60 in the bottom of the reservoir 22. A substantially rigid, perforated cylindrical defoamer retainer 62 is supported on the base plate 58 and extends to the plate 40. The upper end of the defoamer retainer 62 is adapted to fit around an annular support 64 depending from the underside of the plate 40. Blood passes through the tube 48 into the defoamer section 38. The blood can then pass through the defoamer retainer 62, whereby it is defoamed when it passes through the defoamer mesh sock 52. The entire unit 34 is surrounded by a woven sock 66.

As noted above, blood can be separately provided to the filtration section 36 or to the defoaming section 38. As shown in FIG. 6, the lid 24 includes a first port means, comprising at least one opening 68, aligned with the open mouth of the funnel-shaped member 42. Thus, blood that passes through opening 68 of the first port means is provided to the filtration section 36. Blood that is recovered in surgery from suctioning the surgical area must be filtered before it can be returned to the blood stream; this blood is provided to the first port means. The lid 24 also includes a second port means, comprising at least one opening 70. The opening 70 is aligned with a collector 72, which discharges to the tube 48. Thus, blood that passes through the opening 70 of the second port means is provided to the defoamer section 38. Blood that is collected directly from the patient's venous system generally does not have to be filtered. However this blood does tend to froth and must be defoamed before it can be returned to the blood stream; this blood is provided to the second port means.

According to the first embodiment of this invention, the apparatus 20 includes a first connector block 74, alignable with the first port means, for adapting the apparatus 20 for use during surgery, and a second connector block 76 alignable with the first port means, for adapting the apparatus for use after surgery. The apparatus 20 further includes first mounting means for mounting the first and second connector blocks 74 and 76 on the lid 24 of the reservoir 22 with the first connector block 74 initially aligned with the first port means to allow the reservoir to be used during surgery. The first mounting means allows the first connector block 74 to be moved out of alignment with the first port means, and allows the second connector block 76 to be moved into alignment with the first port means so that the apparatus 20 can be used after surgery. Specifically, the first connector block 74 is adapted to facilitate the delivery of blood, collected during surgery and needing filtration, to the first port means. The second connector block 76 is adapted to facilitate the delivery of blood collected after surgery and needing filtration, to the first port means.

The apparatus 20 further includes a third connector block 78 alignable with the second port means for adapting the apparatus 20 for use during surgery, and a fourth connector block 80 alignable with the second port means for adapting the apparatus 20 for use after surgery. The apparatus 20 further includes second mounting means for mounting the third and fourth connector blocks 78 and 80 on the lid 24 of the reservoir 22 with the third connector block 78 initially aligned with the second port means to allow the reservoir to be used during surgery. The second mounting means allows the third connector block 78 to be moved out of alignment with the second port means and allows the fourth connector block 80 to be moved into alignment with the second port means, so that the apparatus 20 can be used after surgery. Specifically, the third connector block 78 is adapted to facilitate the delivery of venous blood, collected during surgery and needing defoaming, to the second port means. The fourth connector block 80 is adapted to close the second port means after surgery because venous blood is no longer returned to the reservoir 22 after surgery is completed.

The first connector block 74, which is shown best in FIGS. 2 and 6, comprises a plurality of connectors or connection devices 74a, 74b, 74c, 74d, 74e, 74f, and 74g. Each of these connectors is adapted to make a connection with equipment used during surgery. For example, connectors 74a, 74b, 74c, and 74d are adapted to connect to surgical field suction devices in order to scavenge lost blood from the wound area; connector 74e is adapted to connect to a luer syringe in order to add drugs; connector 74f is adapted to connect to a luer syringe in order to sample the suctioned blood; and connector 74g is adapted to connect to a prime solution container in order to prime the filter portion 36 of the reservoir 22.

In this first preferred embodiment, all of the connectors 74a-74g communicate with each other, and with the single opening 68 of the first port means. A gasket 82 is mounted in an annular recess in the bottom of the first connector block 74 to seal with the first port means when the first connector block 74 is aligned therewith. (Alternately, the gasket 82 could be mounted in a recess in the lid 24, adjacent port means.) However, the first port means could comprise more than one opening. In this case, not all of the connectors of the first connector block 74 would have to communicate, and thus first connector block 74 would permit separate connections to be made with the reservoir 22. Of course, separate gaskets 82 could be provided on the first connector block 74 (or on the lid 24) to seal each connection.

Figures 10, 11, 12, 13:
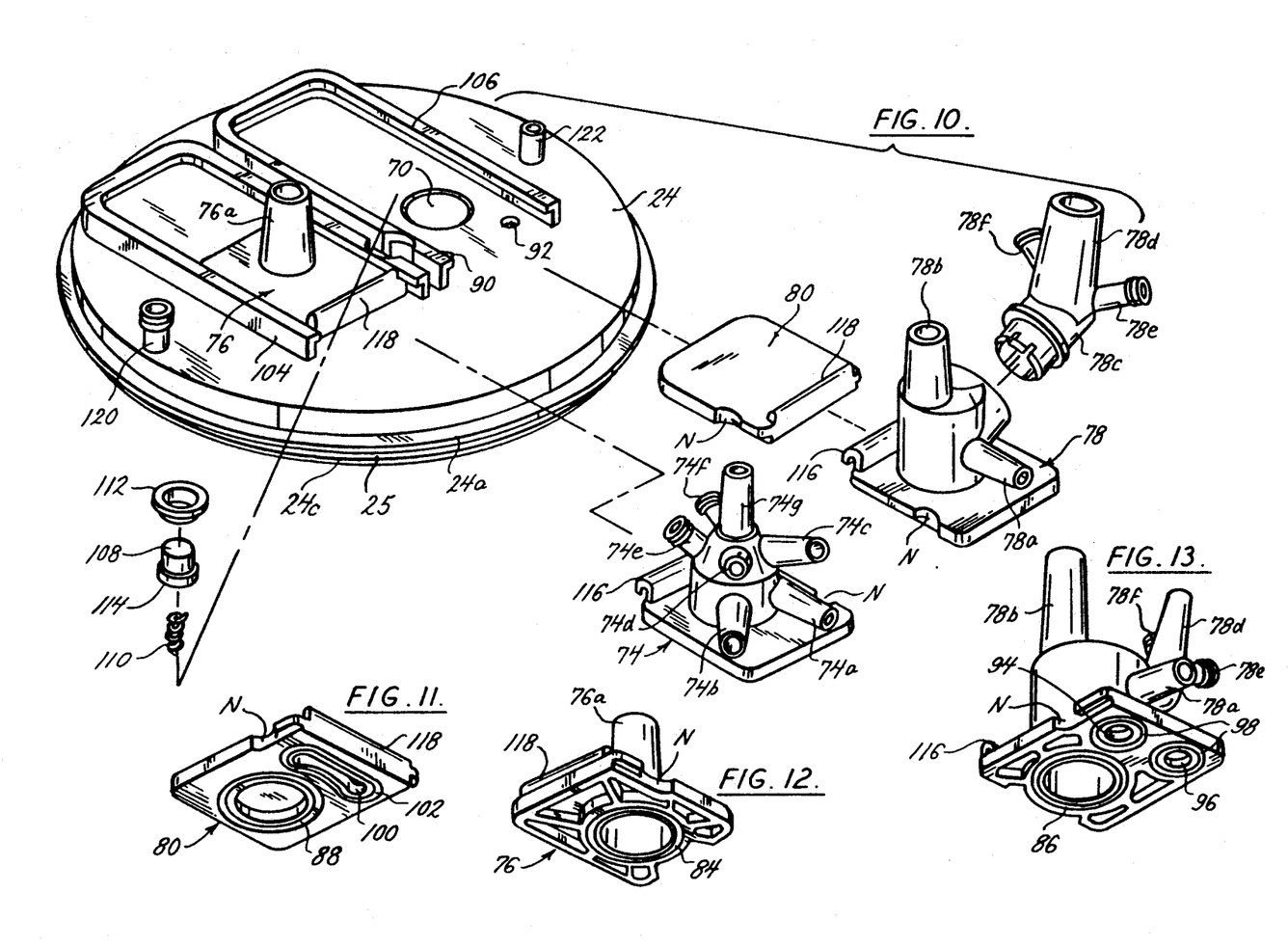
FIG. 10 is an exploded perspective view of the first embodiment.
FIG. 11 is a perspective view from below of the fourth device of the first embodiment.
FIG. 12 is a perspective view from below of the second device of the first embodiment.
FIG. 13 is a perspective view from below of the third device of the first embodiment.

The second connector block 76, which is shown best in FIGS. 2, 10, and 12, comprises a single connector or connection device 76a. The connector 76a is adapted to make a connection used after surgery, for example, to a chest drainage tube to collect the blood from the surgical wound. A gasket 84 is mounted in an annular recess in the bottom of the second connector block 76 to form a seal with the first port means when the second connector block 76 is aligned therewith. (However, if gasket 82 is mounted in lid 24, no gasket 84 is needed in the second connector block 76.)

The third connector block 78, which is shown best in FIGS. 2, 10, and 13, comprises a plurality of connectors 78a and 78b, and a swivel member 78c pivotally mounted in an opening in the third connector block 78, and having three additional connectors 78d, 78e, and 78f. Each of these connectors 78a, 78b, 78d, 78e, and 78f is adapted to make a connection with equipment used during surgery. For example, connector 78a is adapted to connect to the oxygenator in order to allow blood recirculation; connector 78b is adapted to connect to an optional cardiotomy reservoir in order to add additional suctioned blood; connector 78d is adapted to connect to the venous return tube from the patient in order to oxygenate the blood; connector 78e is adapted to connect to a temperature probe in order to monitor venous blood temperature; and connector 78f is adapted to connect to a luer syringe for venous blood sampling.

In this preferred embodiment, all these connectors communicate with each other and with the opening 70 of the second port means. A gasket 86 is mounted in an annular recess in the bottom of the third connector block 78 to seal with the second port means when the third connector block 78 is aligned therewith. (Gasket 86 could alternately be mounted in a recess in lid 24 adjacent to opening 70 of second port means.) However, the second port means could comprise more than one opening. In this case, not all of the connectors of the third connector block 78 would have to communicate, and thus the third device 78 would permit separate connections to be made with the reservoir 22. Of course, separate gaskets 86 could be provided on the third connector block (or on the lid 24) to seal each connection.

The fourth block 80, which is best shown in FIGS. 10 and 11, has no connectors. The fourth block 80 serves to close the second port means after surgery. A gasket 88 is mounted in an annular recess in the bottom of the fourth block 80, to form a seal with the second port means when the fourth block 80 is aligned therewith. (However, if gasket 86 is mounted in lid 24, no gasket 88 is needed in block 80.)

As discussed above, the reservoir 22 is in fact divided into several sections or chambers which during use of the apparatus 20 can be at different pressures. For example one chamber could be considered to be inside the unit 34, and the other chamber could be considered to be outside the unit 34. At least one of the first and second port means, and in this first preferred embodiment the second port means, can comprise vent holes 90 and 92, each in communication with a different chamber (for example, one communicates with the filtration section 36 and the other communicates with the interior of the reservoir 22 outside the filtration section 36 or one communicates with the defoaming section 38 and the other communicates with the interior of the reservoir 22 outside the defoaming section 38).

Sometimes it may be desirable that these chambers be isolated, but at other times it may be desirable that the chambers communicate. Thus, one of the blocks may include means for sealing each of the vent holes 90 and 92, and another of the blocks may include means for allowing these vent holes to communicate. In this preferred embodiment, as best shown in FIG. 13, the third block 78 has two recesses 94 and 96 in its underside surface, each of which is surrounded by a gasket 98 held in an annular recess in the bottom surface of the third block 78. When the third block 78 is aligned with the second port means, the recesses 94 and 96 align with the vent holes 90 and 92 to close and isolate the vent holes. As best shown in FIG. 11, the fourth block 80 has a large, kidney-shaped recess 100 therein, surrounded by a gasket 102. When the fourth block 80 is aligned with the second port means, the recess 100 is aligned with the vent holes 90 and 92 and allows them to communicate, for example to equalize the pressure in the two chambers with which the vent holes communicate. In this first preferred embodiment the vent holes 90 and 92 communicate with the defoamer section 38 and the interior of the reservoir 22, respectively. These are isolated by the third block 78 during surgery, and connected by the fourth block 80 after surgery.

The first, second, third, and fourth blocks 74, 76, 78, and 80, respectively, are slidably mounted on the lid 24 of the reservoir 22. The first mounting means comprises opposing, parallel tracks 104 between which the first and second blocks 74 and 76 are slidably mounted, and the second mounting means comprises opposing, parallel tracks 106 between which the third and fourth blocks 78 and 80 are slidably mounted. In this first preferred embodiment, the first mounting means comprises a first generally U-shaped track 104, having a closed bottom end, two generally parallel legs, and an open top end. As best shown in FIG. 2, initially the second block 76 is positioned between the legs of the "U" adjacent the closed end, and the first block 74 is positioned between the legs of the "U" adjacent the open end. The second mounting means comprises a second generally U-shaped track 106, having a close bottom end, two generally parallel legs, and an open top end. As best shown in FIG. 2, initially the fourth block 80 is positioned between the legs of the "U" adjacent the closed end, and the third block 78 is positioned between the legs of the "U" adjacent the open end. In cross-section the tracks 104 and 106 have a generally inverted "L" shape, with a vertically extending sidewall for retaining the blocks between them, and a horizontally extending rim for retaining the blocks against the lid 24. The first and second U-shaped tracks 104 and 106 are preferably positioned side-by-side on the reservoir 22.

The apparatus 20 preferably also comprises means for releasably locking the blocks in position when each is aligned with its respective port means. In this first preferred embodiment, the releasable locking means comprises a detent or button 108, operable between an extended position in which the button 108 engages the block aligned with the port means, and a depressed position in which the button 108 does not engage the block aligned with the port means. The button 108 is preferably mounted in the space between the tracks 104 and 106 on the lid 24 thus, a single button 108 can simultaneously secure two blocks. The tracks 104 and 106 have a cut out so that the button 108 can engage blocks mounted in the tracks. The button 108 is resiliently biased to its extended position by a spring 110. The button is retained in the recess by an annular bezel 112 which engages a projecting rim 114 on the body of the button 108. Each of the blocks 74, 76, 78, and 80 may have a notch N therein to engage the button.

The apparatus 20 preferably further comprises means for releasably interlocking the first and second blocks 74 and 76 so that the first and second blocks move with each other in the track 104, and means for releasably interlocking the third and fourth blocks 78 and 80 so that the third and fourth blocks move with each other in the track 106. This simplifies the conversion of the apparatus 20, and prevents the port means from becoming uncovered. In this preferred embodiment, the first and third blocks 74 and 78 have an inverted channel 116 on their respective rear edges that is adapted to engage an upstanding lip 118 on the front edges of the second and fourth blocks 76 and 80, respectively. Thus as the first block 74 is moved out of alignment with the first port means, the second block 76 is moved into alignment with the first port means. Since the first block 74 is no longer constrained in the track 104, it can be lifted and simply removed. Likewise, as the third block 78 is moved out of alignment with the second port means, the fourth block 80 is moved into alignment with the second port means. Since the third block 78 is no longer constrained in the track 106, it can be lifted and simply removed. The lid 24 of the reservoir 22 includes two other connectors 120 and 122. Connector 120 is adapted for connection to a priming fluid container in order to prime the non-filtered, outer reservoir chamber or vent or wall suction after surgery, and connector 122 is adapted for limiting wall vacuum with a relief valve.

Figure 14:
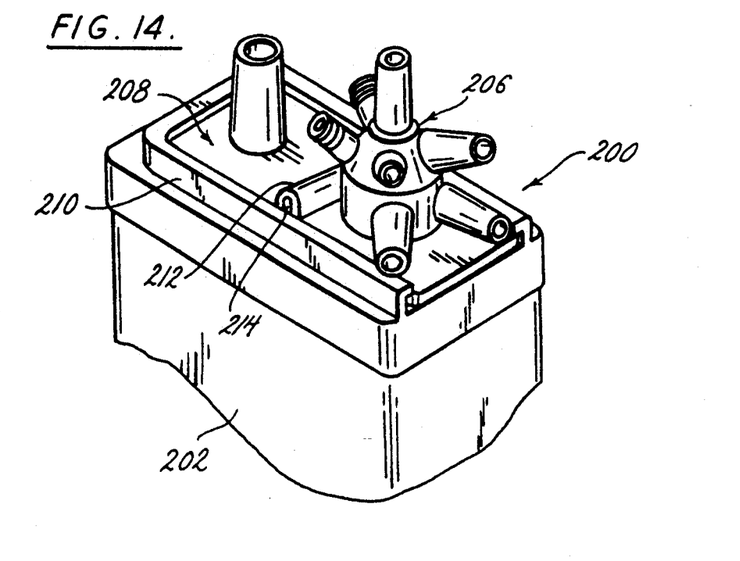
FIG. 14 is a perspective view of a second embodiment of the present invention.

A second embodiment of this invention, indicated generally as 200, is shown in perspective in FIG. 14. The apparatus 200 is adapted for handling a patient's blood during a medical procedure and is convertible for use in blood collection after the procedure. The apparatus 200 is similar in construction to apparatus 20, however, instead of four blocks, there are only two blocks mounted on the apparatus. The apparatus 200 comprises a reservoir 202, having a port means comprising at least one opening therein. The apparatus further comprises a first block 206, alignable with the port means, for adapting the reservoir for use during the procedure, and a second block 208, alignable with the port means, for adapting the reservoir 202 for use after the procedure. The apparatus 200 has a mounting means for mounting the first and second blocks 206 and 208 on the reservoir 202 with the first block initially aligned with the port means to allow the reservoir 202 to be used during the medical procedure. The mounting means allows the first block 206 to be moved out of alignment with the port means and allows the second block 208 to be moved into alignment with the port means to allow the reservoir 202 to be used after the medical procedure.

The first block 206 is similar in construction to first block 74, described above, and preferably comprises at least one connector that communicates with the opening when the first block 206 is aligned with the port means. The connector allows a connection to be made with the reservoir 202 so that the apparatus 200 can be used during the medical procedure. The second block 208 is similar in construction to the second block 76, described above, and likewise comprises at least one connector that communicates with the opening when the second block 208 is aligned with the port means. The connector allows a connection to be made with the reservoir 202 to use the apparatus 200 after the medical procedure. The port means may comprise a plurality of openings, and at least one of the blocks may comprise a plurality of connectors, each communicating with one of openings when its respective block is aligned with the port means, to allow separate connections to be made to the reservoir 202.

As described above with respect to the first embodiment, the reservoir 202 may be divided into more than one chamber. In such a case, the port means may comprise a vent hole communicating with each chamber. One of the first and second blocks 206 and 208 could then comprise means for closing the vent holes, and the other of the first and second blocks 206 and 208 comprise means for connecting the vent holes (for example to equalize the pressure between the chambers).

The first and second blocks 206 and 208 are preferably slidably mounted on the reservoir 202. The mounting means preferably comprises opposing, parallel tracks between which the first and second blocks are slidably mounted. As described above with respect to the first embodiment, the mounting means preferably comprises a generally U-shaped track 210 having a closed end, two generally parallel legs, and an open end. The second block 208 is positioned between the legs of the "U" adjacent the closed end, and the first block 206 is positioned between the legs of the "U" adjacent the open end.

The apparatus may further comprise means for releasably locking the first and second blocks in position when each is aligned with the port means. This means may be like the releasable locking means of the first embodiment, comprising a detent or push button like button 108 operable between an extended position in which the push button engages the first and second blocks, and a depressed position in which the push button does not engage the first and second blocks.

Also like the first embodiment, the first and second blocks 206 and 208 may be releasably connected together so that they move together. The first block 206 may have a downwardly facing channel 212 which engages an upwardly projecting lip 214 on the second block 208.

Figure 15:
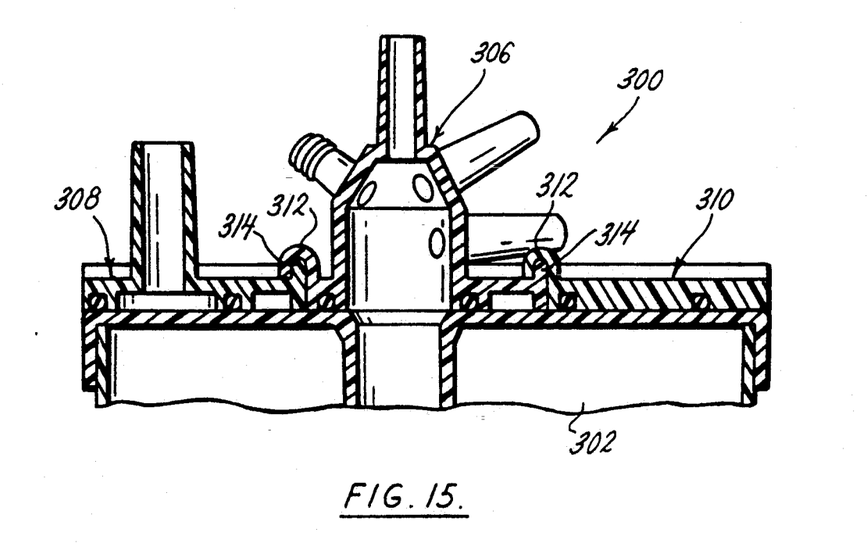
FIG. 15 is a partial cross-sectional view of a third embodiment of the present invention.

A third embodiment of this invention indicated generally as 300 is shown in cross section in FIG. 15. The apparatus 300 is adapted for use in handling a patient's blood during a medical procedure and is convertible for use after the procedure for at least one further use. The apparatus 300 comprises a reservoir 302, having port means therein comprising at least one opening 304. The apparatus further comprises a primary block 306, alignable with the port means, for adapting the reservoir 302 for use during the procedure, and one or more secondary blocks each alignable with the port means for adapting the reservoir 302 for one or more further uses after the procedure. In this third preferred embodiment there are two such secondary blocks 308 and 310. The primary block 306 and the secondary blocks 308 and 310 may be similar in construction to the blocks described in the first and second embodiments. The apparatus 300 includes means for mounting the primary block 306 and the secondary blocks 308 and 310 on the reservoir 302 with the primary block 306 initially aligned with the port means to allow the reservoir 302 to be used during the medical procedure. The mounting means allows the primary block 306 to be moved out of alignment with the port means and allows at least one of the secondary blocks 308, 310, to be moved into alignment with the port means to allow the apparatus 300 to be used after the medical procedure.

The mounting means preferably comprises a pair of generally parallel tracks between which the primary and secondary blocks 306, 308, and 310 are slidably mounted. The tracks are preferably open at both ends so that the primary and second blocks can slide between the tracks in either direction.

In this third preferred embodiment the secondary blocks 308 and 310 are preferably mounted one on either side of the primary block 306 (as shown). However, the secondary blocks 308 and 310 could be mounted on the same side of the primary block 305, if desired. In either event, the primary block 306 and secondary blocks 308 and 310 are preferably releasably secured together so that they move together. For example, the blocks may be provided with interlocking downwardly facing channels 312 and upwardly projecting lips 314.

The blood reservoir 22 (or any of the apparatus of this invention) may be mounted with a bayonet-style mounting consisting of a plurality of generally L-shaped slots 32 for receiving and engaging pins 33 projecting from the device, e.g. blood oxygenator 30, on which the reservoir 22 is mounted. The L-shaped slots 32 have an outer reach 32a extending generally axially of the apparatus, and an inner reach 32b extending generally circumferentially of the apparatus. The apparatus is moved downwardly over the pins 33, so that the pins 33 penetrate into the outer reaches 32a of the slots. The apparatus is then rotated relative to the pins so that pins penetrate into the inner reaches 32b of the slots.

Figure 16:
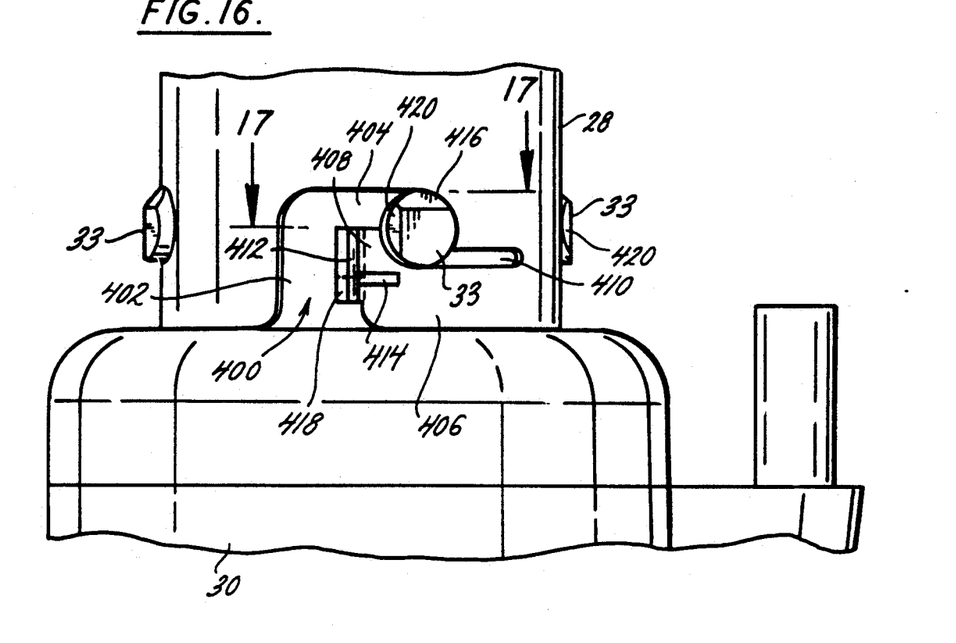
FIG. 16 is a side elevation view of a locking slot for a bayonet mount that can be used with the reservoirs of this invention.
Figures 17, 18:
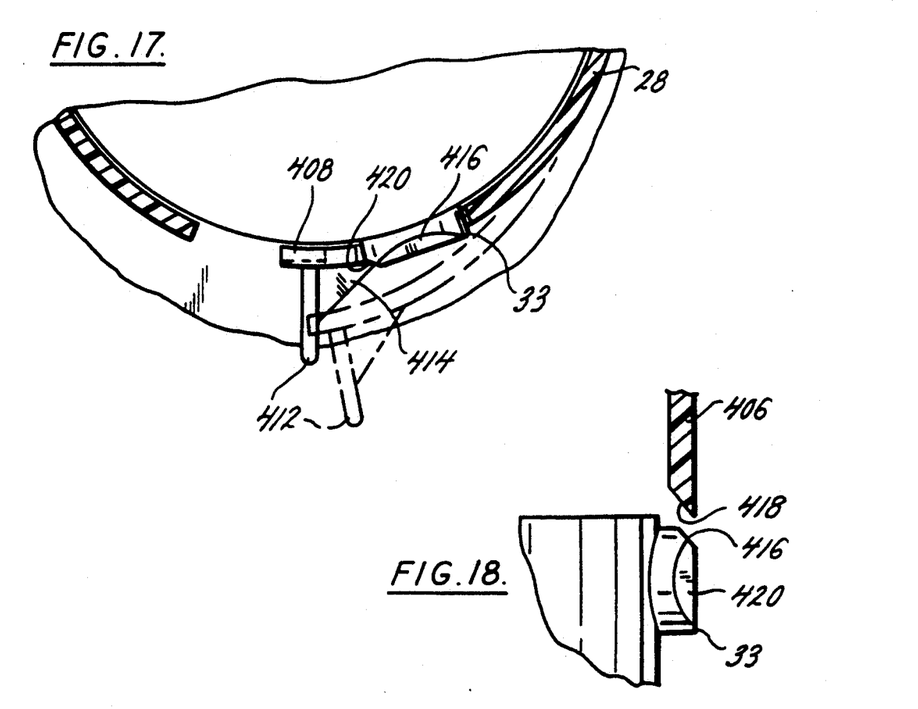
FIG. 17 is a partial cross-sectional view of the locking slot taken along the plane of line 17—17 in FIG. 16.
FIG. 18 is a partial side elevation view showing the camming surfaces on the pin and the tab.

One of these slots 32 is preferably constructed to releasably lock a pin in the inner reach of the slot to prevent the apparatus from being inadvertently dismounted. This releasably lockable slot, indicated generally as 400 in FIGS. 16–18, is likewise generally L-shaped, comprising an outer reach 402 and an inner reach 404. The slot defines a circumferentially extending tab 406. The end of this tab 406 has means, such as projection 408, for engaging and retaining the pin in the inner reach of the slot 400. The tab 406 is dimensioned and configured to be flexible so that the tab 406 can be flexed to pull projection 408 out of engagement with the pin 33. There is preferably an elongate slit 410, extending generally parallel to the tab 406 from the end of the slot 400 to facilitate the flexing of the tab. The end of the slit 410 is generally rounded to reduce stress concentration.

As best shown in FIG. 17, the end of the tab 406 has an outwardly projecting finger grip 412 for facilitating the flexing of the tab. A generally triangular reinforcing web 414 extends between the finger grip 412 and the tab 406.

As best shown in FIG. 18, either the upper portion 416 of the pins 33 or the lower edge 418 of the tab 406, or preferably both, are chamfered so that when the tab and the pin 33 are urged together, the tab is cammed outwardly with respect to the pin so that the tab clear the pin. The reservoir 22 is manipulated so that the pin 33 is aligned with the inner portion of the slot 400. The tab 406 "snaps" back providing a positive audible indication that the reservoir is properly seated and locked into place.

The pins 33 may also have chamfered side edges 420. The chamfered side edges 420 facilitate the disengagement of the projection 408 with the pin 33. Rather than a chamfered top edge and a chamfered side edge, the pins 33 could be made with the entire circumferential edge chamfered. Although only one locking device is provided on the reservoir, all of the pins have the chamfered edges so that no particular orientation is required to secure the reservoir.

Figures 19, 20, 21:
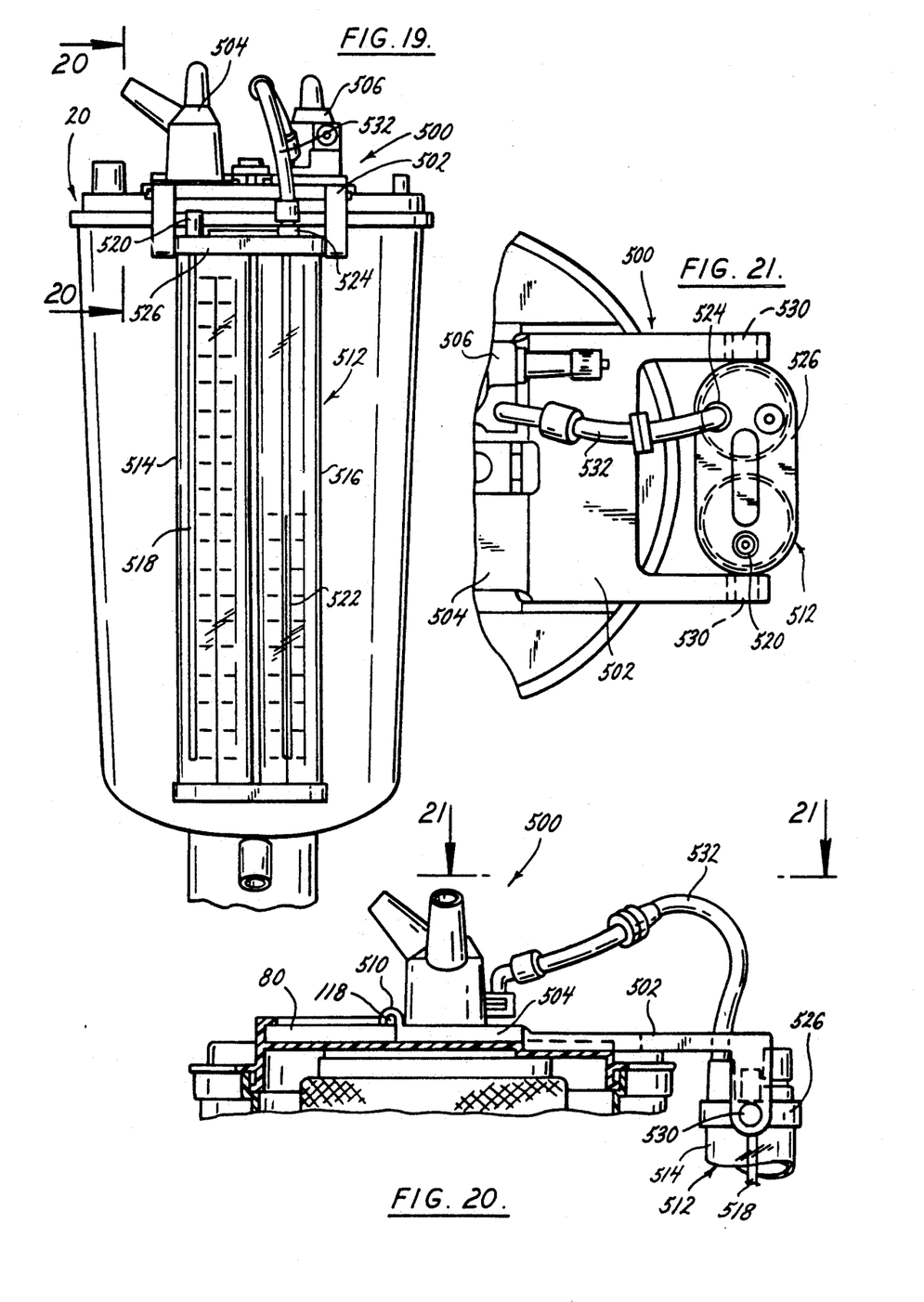
FIG. 19 is a front elevation view of a device with an integral water-seal adapted for use with the first embodiment.
FIG. 20 is a partial side elevation view of the device, taken along the plane of line 20—20 in FIG. 19.
FIG. 21 is a partial top plan view of the device, taken along the plane of line 21—21 in FIG. 20.
Figure 22:
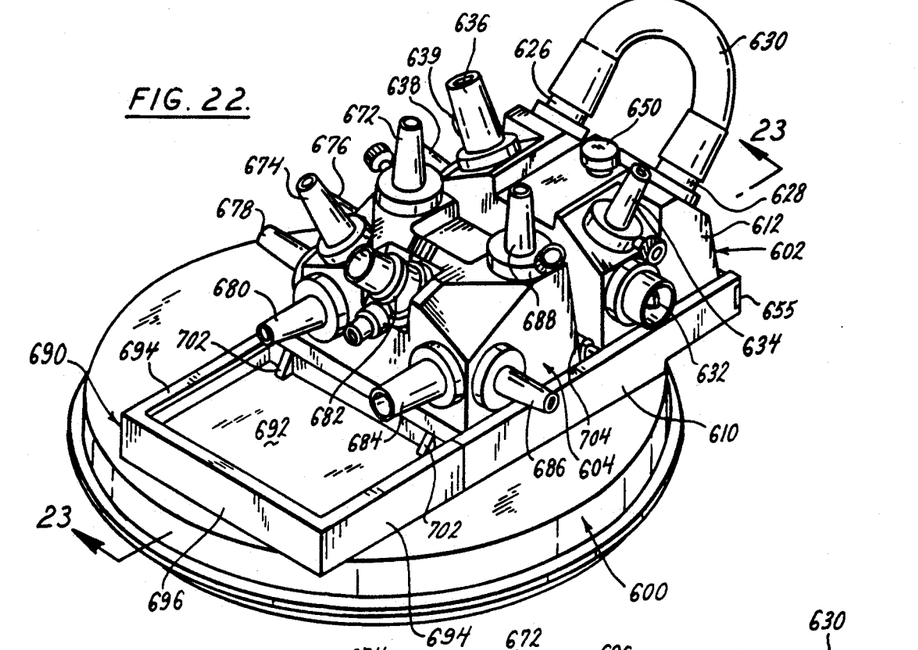
FIG. 22 is a perspective view of a fourth embodiment of this invention, in the form of a lid for a cardiotomy reservoir.

A specialty device with an integral water-seal, adapted for use with the apparatus 20 of the first embodiment, is indicated generally as 500 in FIGS. 19–21. The apparatus 20 can be initially provided with two "blank" blocks like block 80, in the tracks 104 and 106 in alignment with the port means. The device 500 is provided with two blocks, each adapted to be slid into one of the tracks 104 and 106, to displace the blocks 80, and adapt the apparatus 20 for a particular medical function. For example the device 500 could, as shown in FIGS. 19–21, be provided with blocks that perform the same functions as the blocks 74 and 78. However, the specialty device 500 could be provided with some other blocks so that the specialty device 500 can adapt apparatus 20 for some other medical function.

As best shown in FIG. 21, the specialty device 500 comprises a generally U-shaped frame 502. Two blocks 504 and 506 are attached side by side to the bottom of the "U" of the U-shaped frame 502. The blocks 504 and 506 correspond generally to the blocks 74 and 78, described above. The blocks 504 and 506 are sized and spaced so that they can slide into the tracks 104 and 106, respectively, on the lid 24, displacing the blocks 80, aligning with the port means on the apparatus 20, and adapting the apparatus 20 for a particular medical procedure. The blocks 504 and 506 preferably have inverted channels 510 (see FIG. 20), like the inverted channels 116 on the blocks 74 and 78, which are adapted to engage an upstanding lip 118 on the blocks 80, thereby releasably connecting the device 500 to the blocks 80 in the tracks 104 and 106.

The device 500 also comprises a standard water-seal unit 512. As is well known in the art, the water-seal unit 512 comprises two cylinders 514 and 516. A tube 518 extends downwardly from a nipple 520 at the top of cylinder 514. Similarly a tube 522 extends downwardly from a nipple 524 at the top of the cylinders. A passage in cap 526 connects the tops of the cylinders 514 and 516. Water is placed in one or both of the cylinders 514 and 516 to a level that is above the lower ends of tubes 518 and 522. Thus, the water provides a seal between the two nipples 520 and 524.

The water-seal unit 512 has trunions 530 that are journaled between the legs of the U-shaped frame 502. The water-seal unit 512 is thus pivotally mounted in the frame 502, and hangs over the side of the lid 24, alongside the reservoir 22. A tube 532 connects the water-seal unit 512 to the block 506. Thus, device 500 conveniently provides for sterile connections to be made to the block 506 via the water-seal unit 512.

The water-seal unit 512 can be provided pre-charged with sterile water so that the device 500 is ready for immediate use. The device 500 can be quickly installed on apparatus so as to convert it for use in a medical procedure. The prefilled, integral water-seal unit 512 eliminates the time needed to install and fill a separate water-seal. Moreover, it is possible to make preconnections with the blocks 504 and 506 so that the installation of the device 500 simply requires pushing the frame 502 to urge the blocks 504 and 506 into the tracks 104 and 106. The water-seal unit 512 can be replaced, if necessary, by resiliently forcing apart the legs of the U-shaped frame 502 to remove the old water-seal unit, and install a new one.

A forth embodiment of this invention, in the form of a lid 600 for a blood handling apparatus, for example the reservoir 22 of the first embodiment, is shown in FIGS. 22–29. The lid 600 is preferably similar in construction to lid 24, described above, so that it seals with the reservoir 22. According to this embodiment, a first block, for example ICU block 602, is slidably mounted on the lid 600 to adapt the reservoir 22 for a particular function or use, in the case of block 602, for use as a blood collection apparatus in an intensive care unit. One or more other blocks, for example OR block 604 can be releasably installed on the lid 600 to selectively adapt the reservoir 22 for one or more other uses, in the case of OR block 604, for use in a blood oxygenation circuit during heart surgery. As used herein, "OR" refers to operating room.

The lid 600 comprises at least one port means 606 comprising at least one opening 608 communicating with the reservoir 22. In this preferred embodiment there are four openings 608a, 608b, 608c, and 608d (see FIG. 28). A pair of generally parallel tracks 610 are provided on the lid 600 to slidably mount at least one block thereon. This block may be a block to simply occlude the port means 606, or as in this preferred embodiment, it may be an ICU block 602.

The ICU block 602 comprises a hollow dome-like shell 612. A plurality of internal walls 614 divide the interior of the shell 612 into a plurality of compartments 616. In this preferred embodiment there are three walls 614a, 614b, and 614c, that divide the shell into four compartments 616a, 616b, 616c, and 616d (see FIG. 25). The shell 612 is mounted on a base 618, which isolates the compartments 616 from each other. The underside of the base 618 has at least one recessed generally annular groove 620 therein for receiving a sealing gasket 622 so that when the base is properly aligned with the port means 606, a seal is formed between the lid and base encompassing the openings 608 of the port means 606. In this preferred embodiment there are four grooves 620a, 620b, 620c, and 620d, each holding an endless loop sealing gasket 622a, 622b, 622c, and 622d that seals one of the four openings 608a, 608b, 608c, and 608d, respectively, comprising the port means (see FIG. 26).

There are access openings 624 in the base 618 inside at least some of the gaskets, that allow sealed communication between the reservoir 22 and at least some of the compartments 616 in the block 602. In this preferred embodiment there are three access openings 624a, 624c, and 624d, in the base 618 of the ICU block 602, which allow communication between opening 608a and compartment 616a, between opening 608c and compartment 616c, and between opening 608d and compartment 616b. There is no opening inside the gasket 622b, and thus the ICU block 602 effectively seals opening 608b.

The ICU block 602 comprises a plurality of connectors for making connections, via the various internal compartments 616, with the reservoir 22. A first connector 626 to compartment 616a and a second connector 628 to compartment 616c are connected by a piece of tubing 630 to allow pressure equalization between various portions of the reservoir 22. If a portion of the reservoir 22 becomes plugged, blood will be drawn through the tubing 630, providing a visual indication of the blockage. The ICU block 602 also comprises a mushroom-type pressure relief valve 632, well known in the art, that communicates via compartment 616b with the reservoir 22. The valve 632 relieves excess pressure differential when the pressure differential between the interior and the exterior of the reservoir 22 is greater than predetermined maximums. The value 632 is configured to allow gas to escape when the pressure inside the reservoir 22 exceeds the ambient pressure by more than a predetermined maximum. The valve 632 is also configured to allow ambient gas to enter the reservoir 22 when the ambient pressure exceeds the pressure in the reservoir 22 by more than a predetermined maximum. There is also a third connector 634 to compartment 616b, which can be used to connect a vacuum line to the reservoir 22. Finally, there are fourth, fifth, and sixth connectors 636, 638, and 639 to compartment 616a, which can be used to connect chest drainage tubes to the reservoir 22.

Figure 23:
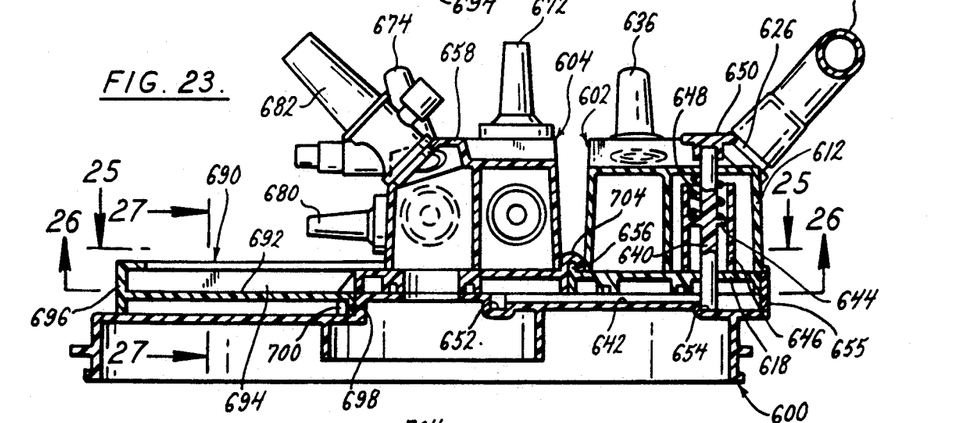
FIG. 23 is a partial vertical cross-sectional view of the lid, taken along the plane of line 23—23 in FIG. 22.
Figure 24:
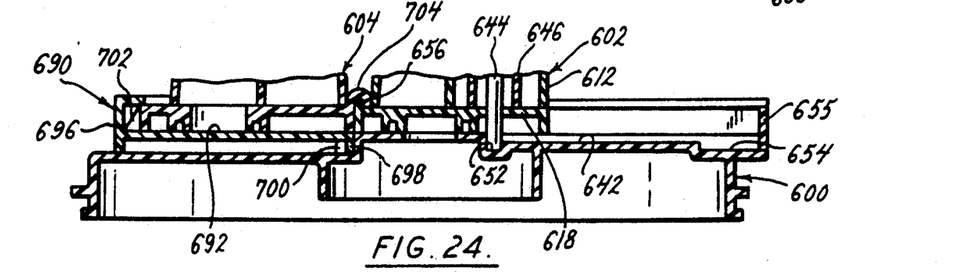
FIG. 24 is a partial vertical cross-sectional view of the lid, similar to FIG. 23 but with one of the connector blocks moved onto a seal tray at the front of the lid.
Figure 25:
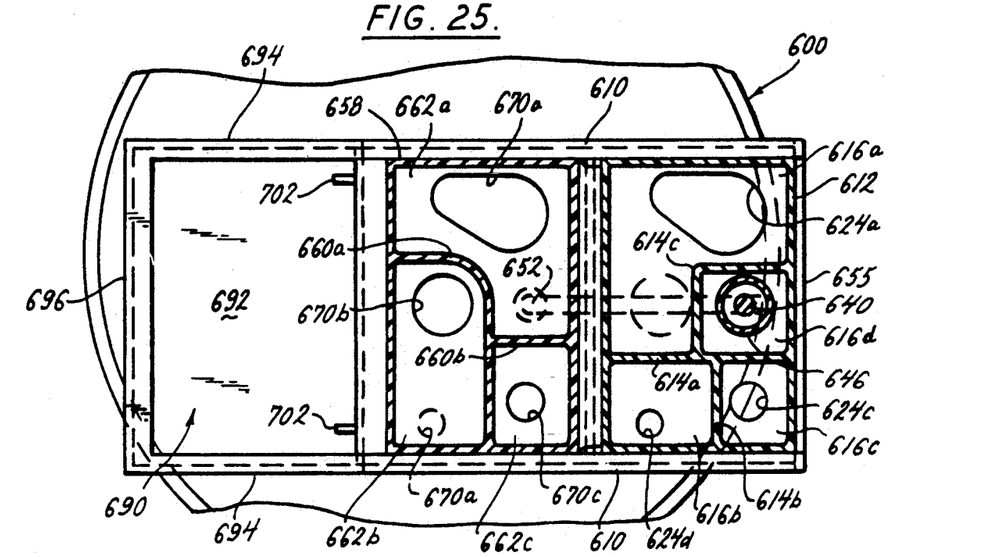
FIG. 25 is a horizontal cross-sectional view of the lid taken along the plane of line 25—25 in FIG. 23.
Figure 26:
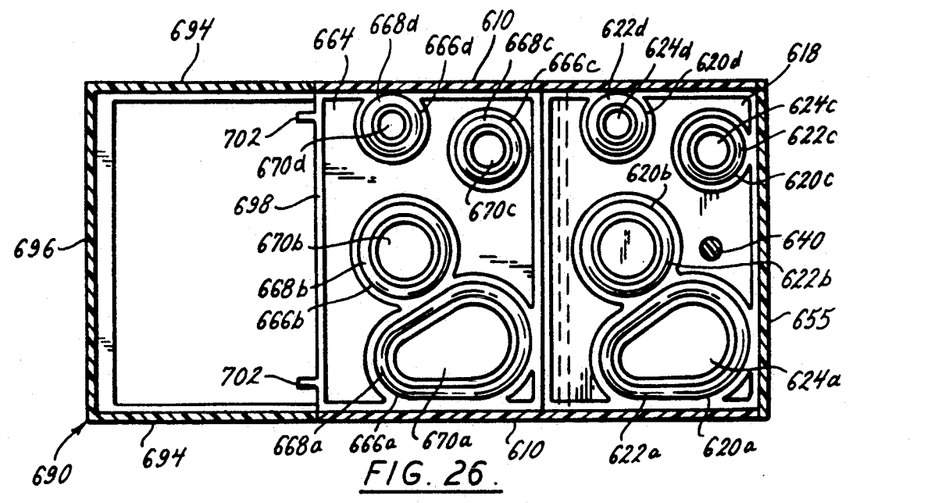
FIG. 26 is a horizontal cross-sectional view of the lid taken along the plane of line 26—26 in FIG. 23.
Figure 27:
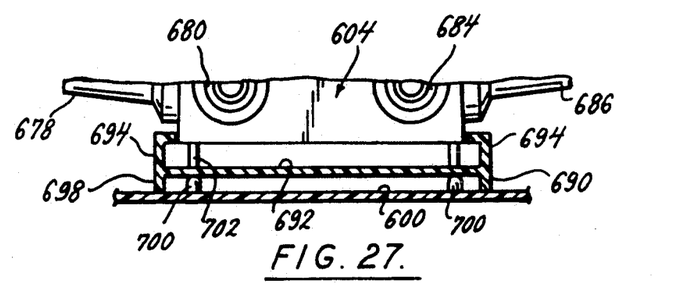
FIG. 27 is a vertical cross-sectional view of the lid, taken along the plane of line 27—27 in FIG. 23.
Figures 28, 29:
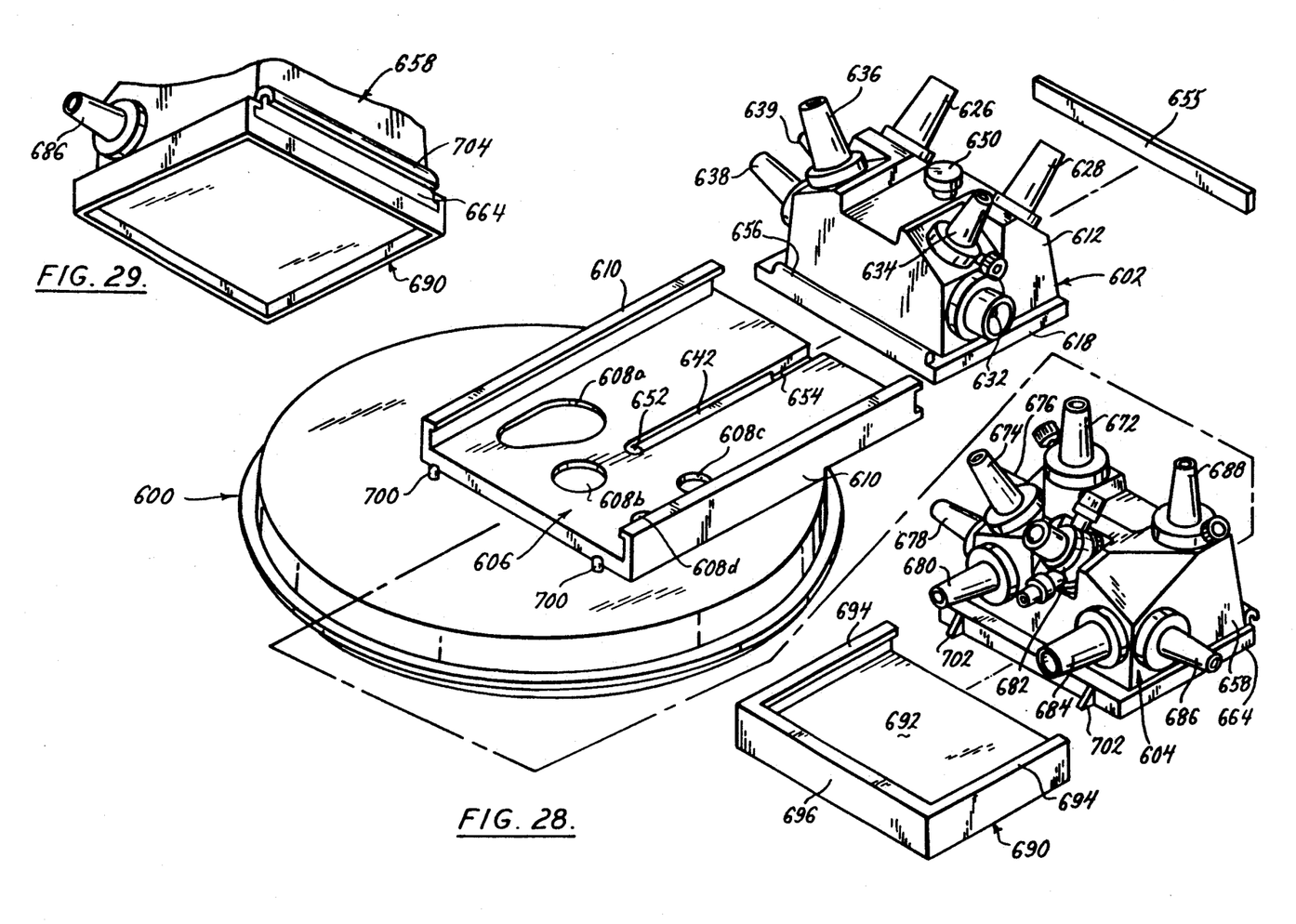
FIG. 28 is an exploded perspective view of the lid.
FIG. 29 is a perspective view from below of a connector block on a seal tray.

The block 602 also includes a spring-biased locking pin 640. The lower end of the locking pin 640 is adapted to fit within and lock in a slot 642 formed in the lid 600. As best shown in FIG. 23, the pin 640 is located in compartment 616d, isolated from the reservoir 22 and thus from exposure to blood. A flange 644 extends radially outwardly from the shaft of the pin 640 to support a sleeve 646 concentrically positioned around the pin 640. A spring 648 compressed between the upper surface of the flange 644 and the top of the shell 612 to resiliently bias the pin 640 downwardly into the slot 642. The bottom end of the sleeve 646, serves as a stop, engaging the base 618 and limiting the downward travel of the pin 640. The top of the pin 640 is provided with an enlarged head 650 by which the pin 640 can be conveniently gripped to lift the pin 640 against the bias of the spring 648, and allow the block 602 to be moved. As best shown in FIGS. 23 and 28, the slot 642 has a depression 652 at its forward end, into which the lower end of the pin 640 can extend to lock the block 602 in its forward most position in alignment with the port means 606. The slot 642 also has a depressed section 654 at its rearward end, into which the lower end of the pin 640 can extend to lock the block 602 in its rearward most position. The lid 600 is assembled by sliding the block 602 into the tracks 610 at the rearward end of the slot 642. A bar 655 is secured across the tracks 610 to retain the block 602 in the tracks 610.

The forward end of the base 618 has an upstanding lip 656 to engage other blocks, as described below.

The lid 600 is constructed and adapted so that other blocks can be selectively mounted thereon, in alignment with the port means 606, to adapt the reservoir 22 for various functions. As shown in this preferred embodiment, one such possible block is OR block 604.

The OR block 604 is generally similar in construction to ICU block 602. The OR block 604 comprises a hollow dome-like shell 658. A plurality of internal walls 660 divide the interior of the shell 658 into a plurality of compartments 662. In this preferred embodiment there are two walls 660a and 660b that divide the shell into three compartments 662a, 662b, and 662c (see FIG. 25). The shell 658 is mounted on a base 664, which isolates the compartments 662 from each other. The underside of the base 664 has at least one recessed generally annular groove therein for receiving a sealing gasket so that when the base 664 is properly aligned with the port means 606, a seal is formed between the lid 600 and base 664 encompassing the openings 608 comprising the port means 606. In this preferred embodiment there are four grooves 666a, 666b, 666c, and 666d, each holding an endless loop sealing gasket 668a, 668b, 668c, and 668d that seals one of the four openings 608a, 608b, 608c, and 608d, respectively, comprising the port means (see FIG. 26).

There are openings 670 in the base 664 inside at least some of the gaskets, that allow sealed communication between the reservoir 22 and at least some of the compartments 662 in the block 604. In this preferred embodiment there are three openings 670a, 670b, and 670c in the base 664 of the OR block 604, which allow communication between opening 608a and compartment 662a, between opening 608b and compartment 662b, and between opening 608c and compartment 662c. There is no opening inside the gasket 668d and thus the OR block 604 effectively seals the opening 608d.

The OR block 604 comprises a plurality of connectors for making connections, via the various internal compartments 662, with the reservoir 22. There are five connectors 672, 674, 676, 678, and 680 connected to compartment 662a. The connector 672 is for adding prime solution directly into the filtered area of reservoir 22. Connectors 674, 676, 678, and 680 are for attachment to blood suction lines from the surgical site. There are three connectors 682, 684, and 686 connected to compartment 662b. The connector 682 is for attaching a venous return blood line from the patient to compartment 662b. The connector 684 is for optionally attaching a drain tube from cardiotomy reservoir to compartment 662b. The connector 686 is for attachment of a blood and/or prime tube from the outlet side of the blood oxygenator (typically the recirculation port) to compartment 662b. There is one connector 688 connected to compartment 662c. This allows both the priming of the reservoir 22 outside the filter and venting the reservoir 22.

The OR block 604 is slidably mounted on a seal tray 690. The seal tray 690 has a bottom surface 692 for sealingly engaging the gaskets on the base of the block 604. The seal tray 690 preferably has raised side rails 694, alignable with the tracks 610 on the lid 600, and a raised back 696 to retain the block on the seal tray 690. There is a depending lip 698 around the seal tray 690, the front portion of which is adapted to fit over raised bosses 700 on the lid 600 when the seal tray 690 is aligned with the tracks 610. The lip 698 and the bosses 700 cooperate to retain the seal tray 690 in position aligned with the tracks 610 against side-to-side movement or movement away from the tracks. The base 664 of the block 604 has feet 702 adapted to engage the seal tray 690 when the block 604 is in the tracks 610, holding the seal tray 690 down against vertical movement, and cooperating with the lip 698 and bosses 700 to retain the seal tray 690 in alignment with the tracks 610 while the block 604 is in the tracks 610.

The forward edge of the base 664 of the block 604 has an inverted channel 704 adapted to engage the raised lip 656 on the base 618 of block 602 so that the two blocks 602 and 604 move together in the tracks 610.

It is contemplated that a plurality of various types of connector blocks similar to OR blocks 604 might be mounted on a plurality of seal trays similar to seal tray 690 so that the medical practitioner is able to choose from the different types of connector blocks the one or ones that are suitable for the procedure. For example, a connector block or blocks similar to blocks 504 and 506 may be provided on a seal tray similar to seal tray 690 to allow for the selection of a specialty device having a water seal unit 512, while a different seal tray has a connector block similar to OR block 604 mounted thereon.

OPERATION

In operation, the apparatus 20 of the first embodiment is prepared for use by making the appropriate connections with the first block 74 to deliver suctioned blood collected during surgery to the filtering section 36 of the unit 34. Similarly, the appropriate connections are made with the third block 78 to deliver venous blood collected during surgery to the defoaming section 38 of the unit 34. The blood collected in the reservoir 22 is removed through outlet 26, and returned to the patient with a pump as is well known in this art. After the surgery is completed, rather than disconnecting all of the lines to the first and third blocks 74 and 78, and capping their respective connectors, 74a, 74b, 74c, 74d, 74e, 74f, 74g, 78a, 78b, 78d, 78e, and 78f as had to be done with prior devices, the push button 108 is simply pressed and the first block 74 is slid out of the track 104, which simultaneously brings the second block 76 into alignment with the first port means. Similarly, the third block 78 is slid out of the track 106 which simultaneously brings the fourth block 80 into alignment with the second port means.

With the second and fourth blocks 76 and 80 aligned with the first and second port means, respectively, the apparatus 20 is now adapted for post-procedure use as a pleura drainage reservoir. A chest drainage tube can be connected to the connector 76a of the second block 76, so that blood suctioned from the surgical wound after surgery is filtered and stored in the reservoir 22. The fourth block 80 blocks the second port means, which is not needed because all the post procedure blood should be filtered. The fourth block 80 also equalizes the pressure within the chambers in the reservoir 22 as described above.

In using the apparatus 200 of the second embodiment, the procedure is similar to that with respect to the first embodiment. Appropriate connections are made to the first block 206 to use the apparatus 200 during the medical procedure. After the procedure, the connections don't have to be disconnected, nor do the connectors have to be capped. The first block 206 is slid out of the track 210 and the second block 208 is simultaneously brought into alignment with the port means. The apparatus 200 is thus adapted for its post procedure use. A connection is made with the second block 208 and the apparatus 200 is ready for post procedure use.

In using the apparatus 300 of the third embodiment, the procedure is similar to that with respect to the first and second embodiments. Appropriate connections are made to the primary block 306 to use the apparatus 300 during the procedure. After the procedure, the connections may be disconnected for convenience, but the connectors do not have to be capped. The primary block 306 is simply slid to the left or to the right (as shown in FIG. 15) to bring the appropriate secondary block 308 or 310 into alignment with the port means. The third embodiment could even be arranged so that both of the secondary blocks 308, 310 are on the same side of the primary block 306. Thus one or more secondary blocks can be successively used so that the apparatus 300 is used in more than one subsequent procedure, or used in a subsequent procedure and closed.

The specialty device 500 allows the apparatus 20 to be quickly adapted for use in a medical procedure where it is desirable to establish a sterile water seal. The operator simply aligns the blocks 504 and 506 with the tracks 104 and 106, engages the inverted channels 510 over the upstanding lips 118 on the blocks 80, depresses the button 108, and urges the device 500 forwardly. The blocks 504 and 506 slide forwardly into the tracks 104 and 106, displacing the blocks 80 and aligning with the port means. Connections can then be made to the blocks 504 and 506, and the apparatus 20 can be used in a medical procedure. (Alternatively, the connections can be made to the blocks 504 and 506 before the specialty device 500 is installed on the apparatus 20, thus speeding up the adaptation of the apparatus 20 for the medical procedure.)

When the procedure is over, and it is desired to disassemble the apparatus 20, or convert it to another use, the button 108 can be depressed, and the specialty device 500 pulled from the apparatus 20. Because of the engagement between the blocks 504 and 506 and the blocks 80, the retraction of the device 500 pulls the blocks 80 back over the port means to close it. When the blocks 504 and 506 are clear of the tracks 104 and 106, the inverted channels 510 on the blocks 504 and 506 are lifted off of the upstanding lips 118, separating the specialty device 500 from the apparatus 20.

Another specialty device 500 can be installed on the apparatus 20, or the apparatus 20 otherwise adapted for a further use.

The lid 600 of the fourth embodiment of this invention is adapted to receive different functional blocks to adapt the apparatus to different medical functions. As shown in this preferred embodiment, the fourth embodiment is initially set up for use in an intensive care unit, with the lid 600 mounted on a reservoir 22 and ICU block 602 locked in place over the port means 606. If it were desired to adapt the reservoir 22 for use in surgery, an OR block 604, on a seal tray 690, would be aligned with the tracks 610, with the lip 698 on the seal tray 690 engaging the bosses 700 on the lid 600. The lip 698 and the bosses 700 help to align the seal tray 690 with the tracks 610, and to hold the seal tray 690 in place. As the seal tray 690 is put into place, the inverted channel 704 on the base 664 of the OR block 604 fits over the raised lip 656 on the base 618 of the ICU block 602.

The button 650 is then lifted, to pull the pin 640 out of engagement with the recess 652 in the slot 642, allowing the blocks to slide together rearwardly until the OR block 604 is aligned with the port means 606. The blocks 602 and 604 will be locked from further rearward movement by the bar 655, and from forward motion by the engagement of the pin 640 in the recessed portion 654 of the slot 642. The feet 702 projecting from the base 664 of the OR block 604 hold the seal tray 690 in place. Connections can now be made with the various connectors on the OR block 604. Alternatively, the OR block 604 can be pre-connected with the various devices used during surgery, and simply installed on the reservoir 22 when needed.

When the procedure is over, the button 650 can be lifted and the blocks 602 and 604 moved forwardly, to bring the OR block 604 back onto the seal tray 690. When the OR block 604 is back on the seal tray 690, and out of engagement with the tracks 610, the seal tray 690 and OR block 604 can be removed from the lid 600. The seal tray 690 seals the openings 670 in the base 664 of the OR block 604, thereby reducing the risk of spillage and contamination. The ICU block 602 is again locked in position over the port means by the pin 640 engaging recess 652. The lid 600 is ready to receive another block on a seal tray to adapt the reservoir 22 to a further use. The seal tray 690 also acts as a seal against spillage and contamination prior to surgery, for example during construction of the block, attachment of the tubing, and during sterilization and storage.

As various changes could be made in the above constructions without departing from the scope of the invention, it is intended that all matter contained in the above description or shown in the accompanying drawings shall be interpreted as illustrative and not in a limiting sense.

I claim:

1. A connection system for facilitating connections with an apparatus for handling medical fluids, such as blood, to adapt the apparatus for one or more particular uses, the system comprising:
    at least one port means in the apparatus comprising at least one opening in fluid communication with the apparatus;
    at least one connector block, each connector block having at least one access opening for fluid communication with the port means, and at least one connection device for making a connection to the connector block to adapt the apparatus for a particular medical use when the connector block is in communication with the port means of the apparatus;
    track means on the apparatus for movably mounting the connector blocks on the apparatus such that the blocks can be moved into and out of alignment with the port means; and
    a seal tray alignable with the track means and having rail means for slidably mounting a connector block and initially sealing the connector blocks access opening, the seal tray and the track means being so configured that the rail means of the seal tray can be aligned with the track means to allow the connector block to be moved at least partially off of the seal tray onto the track means, thereby to bring the connector block's access opening(s) into alignment with the port means.

2. A system according to claim 1 wherein the connector block remains in contact with its seal tray when the access openings of the connector block are in fluid communication with the port means to hold the seal tray in position relative to the track means.

3. A system according to claim 1 wherein the connector block has a plurality of connection devices.

4. A system according to claim 1 further comprising a lid on the apparatus, the port means and track means being formed in the lid.

5. A system according to claim 4 further comprising a water seal device connected to the connector block.

6. A system according to claim 1 further comprising a plurality of the connector blocks, and one or more additional seal trays each initially having at least one of the connector blocks mounted thereon, the connector blocks including at least one connector block adapted for a different use than another of the connector blocks.

7. A system according to claim 1 further comprising a plurality of connector blocks including at least one connector block adapted for a different use than another of the connector blocks.

8. A system for facilitating connections with an apparatus for handling medical fluids, such as blood, to adapt the apparatus for one or more particular uses, the system comprising:
    at least one port means in the apparatus comprising at least one opening in fluid communication with the apparatus;
    at least one connector block, each connector block having at least one access opening for fluid communication with the port means, and at least one connection device for making a connection to the connector block to adapt the apparatus for a particular medical use when the connector block is in communication with the port means of the apparatus;
    track means on the apparatus for movably mounting the connector blocks on the apparatus such that the blocks can be moved into and out of alignment with the port means; and
    a seal tray for movably mounting a connector block and initially sealing the connector blocks access opening, the seal tray and the track means being so configured that the seal tray can be aligned with the track means to allow the connector block to be moved at least partially off of the seal tray onto the track means, thereby to bring the connector block's access openings into alignment with the port means;
    the track means being adapted to slidably receive the connector block, the system further comprising a first block slidably mounted on the track means, the first block being initially aligned with the port means but being displaceable therefrom by a connector block.

9. A system according to claim 8 further comprising means for releasably locking the first block or connector block mounted on the track means in alignment with the port means.

10. A system according to claim 8 further comprising means for releasably connecting the connector block and the first block so that the connector block and first block move together in the track means.

11. A system according to claim 8 wherein the first block occludes and seals the port means when aligned therewith.

12. A system according to claim 8 wherein the connector block remains in contact with its seal tray when the access openings of the connector block are in fluid communication with the port means to hold the seal tray in position relative to the track means.

13. A system according to claim 8 wherein the connector block has a plurality of connection devices.

14. A system according to claim 8 further comprising a lid on the apparatus, the port means and track means being formed in the lid.

15. A system according to claim 14 further comprising a water seal device connected to the connector block.

16. A system according to claim 8 further comprising a plurality of connector blocks including at least one connector block adapted for a different use than another of the connector blocks.

17. A system according to claim 8 further comprising a plurality of the connector blocks, and one or more additional seal trays each initially having at least one of the connector blocks mounted thereon, the connector blocks including at least one connector block adapted for a different use than another of the connector blocks.

18. A pre-assembled connection assembly adapted for making quick connections with an apparatus for handling medical fluids, such as blood, the apparatus being of the type having a port means including an opening in fluid communication with the apparatus, and a first block movably mounted in a track over the port means; the connection assembly comprising:
    a connector block having at least one access opening for fluid communication with the port means of the apparatus, and at least one connection device for making a connection to the connector block to adapt the apparatus for a particular medical use when the connector block is in communication with the apparatus; and
    a seal tray, adapted to be releasably attached to the track of the apparatus, for slidably mounting the connector block and initially sealing the connector block's access openings, the seal tray being alignable with a track of the apparatus such that the connector block can be slid at least partially off of the seal tray into the track to displace a first block and bring the connector block's access opening into alignment with the port means of the apparatus.

19. A connection assembly according to claim 18 further comprising a water seal device connected to the connector block.

20. A connection assembly according to claim 18 wherein the connector block remains in contact with the seal tray when the access openings of the connector block are in fluid communication with the port means of the apparatus to hold the seal tray in position relative to the track of the apparatus.

21. A connection assembly according to claim 20 wherein the connector block has a plurality of connection devices.

22. A connection assembly according to claim 20 wherein the connector block has at least one foot for holding the seal tray down to retain the seal tray in alignment with the track of the apparatus.

23. A method of making tubing connections with an apparatus for handling medical fluid, such as blood, to facilitate the set up of the apparatus for use in a medical procedure, the method comprising the steps of:
    providing port means including an opening in fluid communication with the apparatus; a first block for sealing the port means; a connector block having an access opening adapted for fluid communication with the port means, and at least one section of tubing extending therefrom in fluid communication with the access opening; track means for slidably mounting the first block and connector block relative to the port means; and a seal tray for slidably mounting the connector block;
    initially maintaining the first block in alignment with the port means to seal the port means, and maintaining the connector block mounted on the seal tray with the seal tray sealing the access opening of the connector block;
    aligning the seal tray with respect to the track means such that the connector block can be moved at least partially off of the seal tray into the track means;
    moving the connector block at least partially off of the seal tray into the track means until the access opening of the connector block is in fluid communication with the port means such that the connector block moves the first block out of alignment with the port means and the first block and connector block maintain the port means sealed until the access opening is in fluid communication with the port means.

* * * * *